US008636710B2

(12) United States Patent
Ellingson et al.

(10) Patent No.: US 8,636,710 B2
(45) Date of Patent: Jan. 28, 2014

(54) FIT MAINTENANCE SYSTEM

(75) Inventors: Daniel Lee Ellingson, Appleton, WI (US); Janet Elaine Collins, Hortonville, WI (US); Sara Jane Wille Stabelfeldt, Appleton, WI (US); Scott Richard Lange, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 485 days.

(21) Appl. No.: 12/417,183

(22) Filed: Apr. 2, 2009

(65) Prior Publication Data

US 2010/0256583 A1 Oct. 7, 2010

(51) Int. Cl.
*A61F 13/20* (2006.01)

(52) U.S. Cl.
USPC ............ 604/386; 604/367; 604/369; 604/389

(58) Field of Classification Search
USPC ............ 604/369, 367, 389, 387, 386, 385.11, 604/390, 391
See application file for complete search history.

(56) References Cited

U.S. PATENT DOCUMENTS

| | | | |
|---|---|---|---|
| 4,699,622 A * | 10/1987 | Toussant et al. | 604/389 |
| 5,407,439 A | 4/1995 | Goulait | |
| 5,599,338 A | 2/1997 | Enloe | |
| 5,851,205 A | 12/1998 | Hisada et al. | |
| 5,858,013 A | 1/1999 | Kling | |
| 6,195,850 B1 | 3/2001 | Melbye et al. | |
| 6,245,697 B1 * | 6/2001 | Conrad et al. | 442/370 |
| 6,329,016 B1 | 12/2001 | Shepard et al. | |
| 6,402,731 B1 | 6/2002 | Suprise et al. | |
| 6,406,466 B1 * | 6/2002 | Pozniak et al. | 604/386 |
| 6,543,099 B1 | 4/2003 | Filion et al. | |
| 6,554,816 B1 | 4/2003 | Olson | |
| 6,632,974 B1 * | 10/2003 | Suzuki et al. | 604/369 |
| 6,911,407 B2 * | 6/2005 | Sherrod et al. | 442/76 |
| 6,918,900 B2 | 7/2005 | Johnson | |
| 7,150,732 B2 | 12/2006 | Yoshida et al. | |
| 7,344,525 B2 | 3/2008 | Linker, III et al. | |

(Continued)

FOREIGN PATENT DOCUMENTS

| CN | 101272754 A | 9/2008 |
|---|---|---|
| EP | 0 233 704 B1 | 7/1992 |

(Continued)

OTHER PUBLICATIONS

Patent Cooperation Treaty Search Report from the International Search Authority, International Application No. PCT/IB2010/051261 dated Jan. 14, 2011.

*Primary Examiner* — Lynne Anderson
*Assistant Examiner* — Bradley Philips
(74) *Attorney, Agent, or Firm* — Kimberly-Clark Worldwide, Inc.

(57) ABSTRACT

An absorbent article includes a fit system having fasteners and friction elements. The fasteners are located in the front waist area and the back waist area and are adapted to fasten the article about the waist of a wearer to define a waist opening, a pair of leg openings, and a pair of overlap regions. The friction elements are located in the overlap regions and are adapted to provide friction between the front waist area and the back waist area in the overlap regions. The friction elements have an upper portion oriented towards the waist opening and a lower portion oriented towards the leg opening. The upper portion and the lower portion have different concentrations of surface treatment, thicknesses, and/or surface areas.

15 Claims, 11 Drawing Sheets

(56) References Cited

U.S. PATENT DOCUMENTS

| | | |
|---|---|---|
| 7,416,545 B1 | 8/2008 | Kline et al. |
| 7,608,070 B2 * | 10/2009 | Chen et al. .................. 604/391 |
| 2002/0095130 A1 | 7/2002 | Seitter et al. |
| 2002/0095132 A1 | 7/2002 | Ashton et al. |
| 2004/0111076 A1 | 6/2004 | Sayama et al. |
| 2005/0177127 A1 | 8/2005 | Ashton et al. |
| 2006/0069380 A1 * | 3/2006 | Chen et al. .................. 604/391 |
| 2007/0066951 A1 | 3/2007 | Lavon et al. |
| 2007/0099531 A1 | 5/2007 | Efremova et al. |
| 2007/0142815 A1 | 6/2007 | Macura et al. |
| 2007/0250029 A1 | 10/2007 | Popp et al. |
| 2009/0069772 A1 | 3/2009 | Sauer et al. |

FOREIGN PATENT DOCUMENTS

| | | |
|---|---|---|
| EP | 1 299 063 B1 | 3/2006 |
| JP | 07-275294 A | 10/1995 |
| JP | 2008-142345 A | 6/2008 |
| WO | WO 02/43637 A1 | 6/2002 |

* cited by examiner

FIT MAINTENANCE SYSTEM

BACKGROUND OF THE INVENTION

Absorbent articles such as diapers, training pants or incontinence garments desirably provide a close, comfortable fit about the wearer and contain body exudates. Disposable absorbent articles can be secured about the wearer by a variety of fastening systems. Conventional diapers have included a front waist portion and a back waist portion that are releasably connected about the hips of the wearer during use by fastening systems such as adhesive tape fasteners or hook and loop fasteners. Typically, when a user dons the article, the hook tabs and the back waist area are lapped over the front waist area of the article and the hook tabs are secured to the loop panel in the front waist area. The front and back waist areas create the waist opening and a portion of the front and back waist areas overlap each other in surface-to-surface contact.

The performance and fit of the absorbent article is typically improved by providing tension around the waist opening and leg openings of the article through the addition of extensible materials. It is desirable for the absorbent article to maintain its initial fastened position during use so as to maintain proper tension and ultimately proper fit. It is also desirable for absorbent articles to resist radial shifting in the overlap region between the front and back waist areas so as to maintain both the desired leg tension and the desired waist tension. This is complicated in that typically the materials that make up the front and back waist areas of absorbent articles have relatively low coefficients of friction when in surface-to-surface contact with one another. Additionally, the dynamic movement of the user's legs can cause additional shifting and the present inventors have observed that diapers shift by a greater amount in the portion of the overlap region proximate the leg opening as compared to the portion of the overlap region proximate the waist opening. In total, this shifting may be undesirable because of actual or perceived loss of fit. In other words, a user may initially attach the diaper about the waist and legs of a wearer in a desired configuration to achieve a desired fit. However, after some use, the configuration may change and the actual and/or perceived fit may be unsatisfactory.

Thus, there exists a need for a fit system to address these and other fit maintenance needs.

SUMMARY OF THE INVENTION

To address the needs discussed above, the present invention includes friction elements in the overlap regions to selectively increase friction and minimize radial shifting.

In one aspect, the present invention provides an absorbent article having a fit system. The fit system includes fasteners and a friction element. The fasteners are located in a front waist area and a back waist area and are adapted to fasten the article about the waist of a wearer to define a waist opening, a pair of leg openings, and a pair of overlap regions. The friction element is located in at least one of the overlap regions and is adapted to provide friction between the front waist area and the back waist area in the overlap region. The friction element has an upper portion oriented towards the waist opening and a lower portion oriented towards the leg opening. The upper portion has a first concentration of surface treatment and the lower portion has a second concentration of surface treatment which is greater than the first concentration.

In some embodiments of this aspect, the upper portion may have a first thickness and the lower portion may have a second thickness which is greater than the first thickness.

In some embodiments of this aspect, the surface treatment may be polyethylene polymer, low-tack adhesive, a cohesive, polyurethanes, rubber, polypropylene elastomer, or a polymer wax.

In another aspect, the present invention provides an absorbent article having a fit system. The fit system includes fasteners and a friction element. The fasteners are located in a front waist area and a back waist area and are adapted to fasten the article about the waist of a wearer to define a waist opening, a pair of leg openings, and a pair of overlap regions. The friction element is located in at least one of the overlap regions and is adapted to provide friction between the front waist area and the back waist area in at least one of the overlap regions. The friction element has an upper portion oriented towards the waist opening and a lower portion oriented towards the leg opening, the upper portion having a first thickness and the lower portion having a second thickness which is greater than the first thickness.

In some embodiments of this aspect, the first thickness may be 0.1 to 3 mm and the second thickness may be 2 to 5 mm. In some embodiments, the upper portion may include a single layer of material and the lower portion may include more than one layer of material. In some embodiments, the thickness of the friction element may be tapered and may increase in thickness in a direction from the upper portion to the lower portion. In some embodiments, the upper portion may have a first coefficient of friction value and the lower portion may have a second coefficient of friction value that is greater than the first coefficient of friction value.

In another aspect, the present invention provides an absorbent article having a fit system. The fit system includes fasteners and a friction element. The fasteners are located in a front waist area and a back waist area and are adapted to fasten the article about the waist of a wearer to define a waist opening, a pair of leg openings, and a pair of overlap regions. The friction element is located in at least one overlap region and is adapted to provide friction between the front waist area and the back waist area in at least one of the overlap regions. The friction element has a lateral direction centerline defining an upper portion and a lower portion. The upper portion is oriented towards the waist opening and the lower portion is oriented towards the leg opening. The entire upper portion defines a first surface area and the entire lower portion defines a second surface area that is greater than the first surface area.

In some embodiments of this aspect, the first surface area may be 100 to 200 mm$^2$ and the second surface area may be 300 to 700 mm$^2$. In some embodiments, the upper portion may have a first thickness and the lower portion may have a second thickness which is greater than the first thickness.

In various embodiments of any aspect, the absorbent article may include two friction elements. The absorbent article may also include an outer cover joined in facing relationship with a bodyside liner and may include an absorbent core located between the outer cover and the bodyside liner. The fasteners may include hook portions in the back waist area and loop portions in the front waist area. The two friction elements may be located on the outer cover in the front waist area in the overlap regions and may have a peel value of less than 1000 grams.

In various embodiments of any aspect, the absorbent article may include friction elements made of open cell flexible polyurethane foam or a foam material selected from the group consisting essentially of: melamines; polyadehydes; polyurethanes; polyisocyanurites; polyolefins; polyvinylchloride;

epoxy foams; ureaformaldehyde; latex foam; silicone foam; fluoropolymer foams; polystyrene foams; and, mixtures thereof.

In various embodiments of any aspect, the waist opening and the leg openings may define a side coverage length and a single friction element may be located in each overlap region and each friction element may have a friction element length that is at least 50% of the side coverage length.

DETAILED DESCRIPTION OF THE DRAWINGS

The fit maintenance system, including the graduated friction elements, of the present invention assist in maintaining proper fit in various absorbent articles. The absorbent articles of the present invention will be described in terms of diapers adapted to be worn by babies about the lower torso. However, the present invention may also be applicable to other absorbent articles such as adult incontinent absorbent articles, children's training pants, feminine care absorbent articles and the like.

Figure 1:
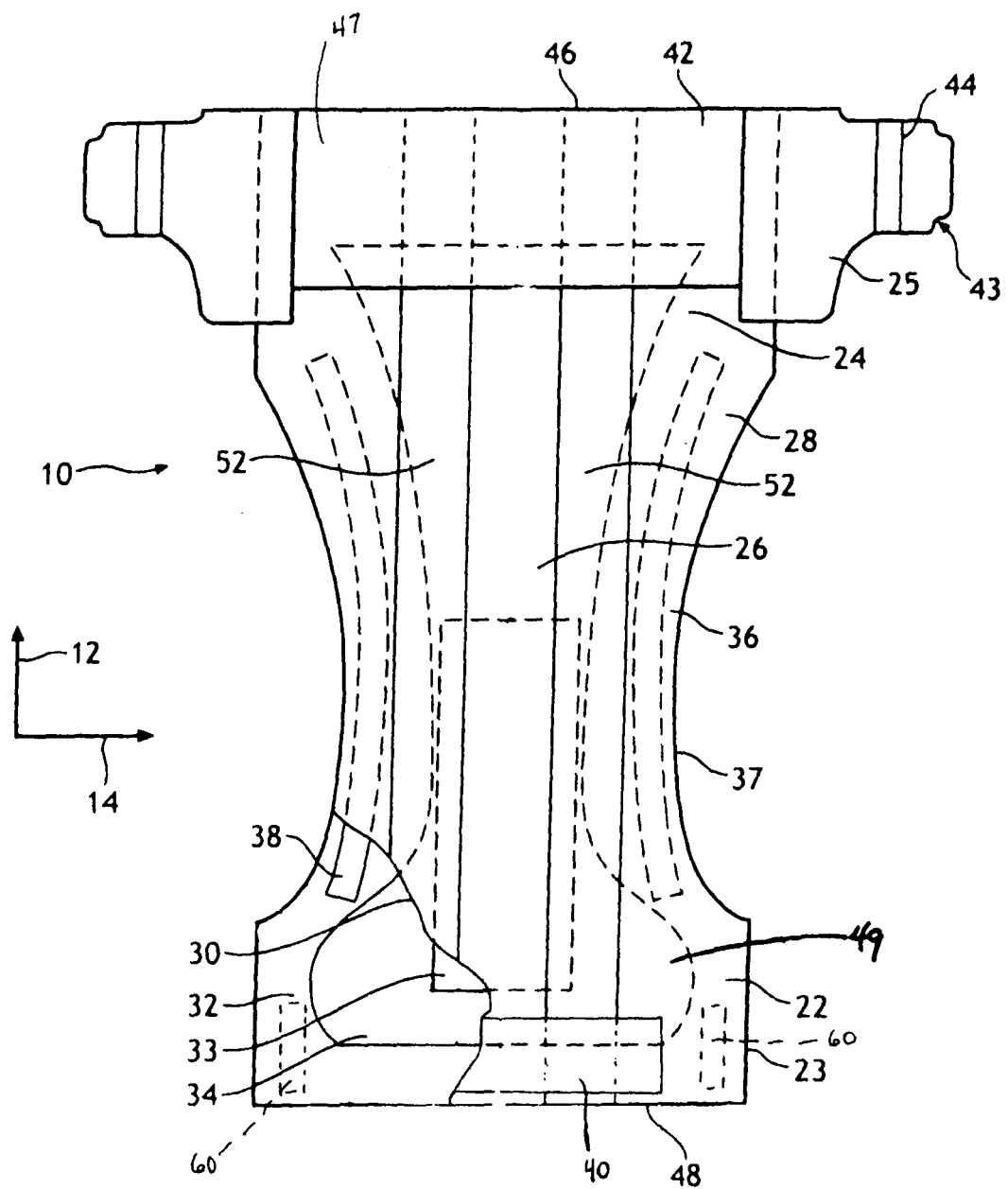
FIG. 1 representatively illustrates a diaper in an unfastened condition with portions cut away to illustrate underlying structures and having the surface which contacts the wearer facing the viewer.
Figure 2:
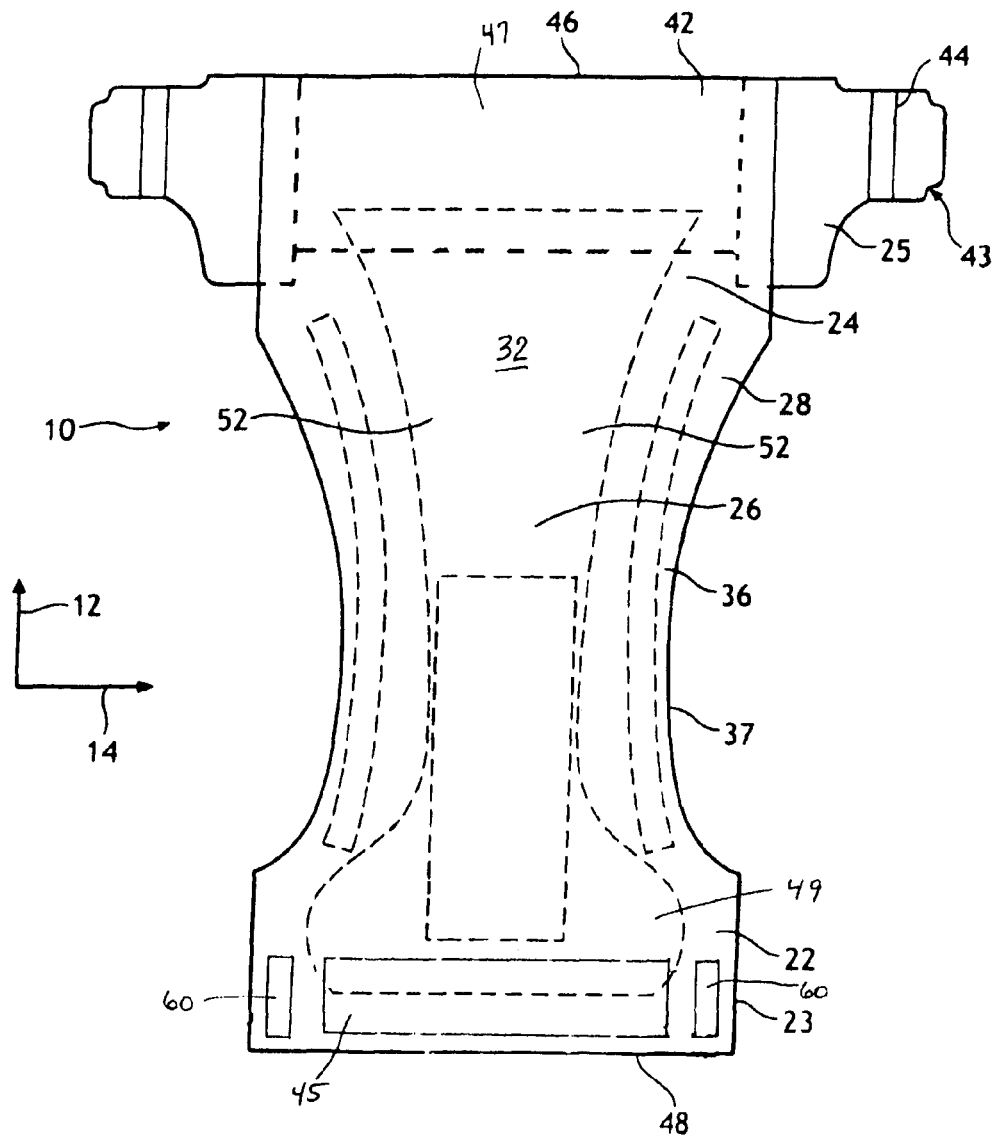
FIG. 2 representatively illustrates the diaper of FIG. 1 in an unfastened condition with the surface which contacts the clothing of the wearer facing the viewer.
Figure 3:
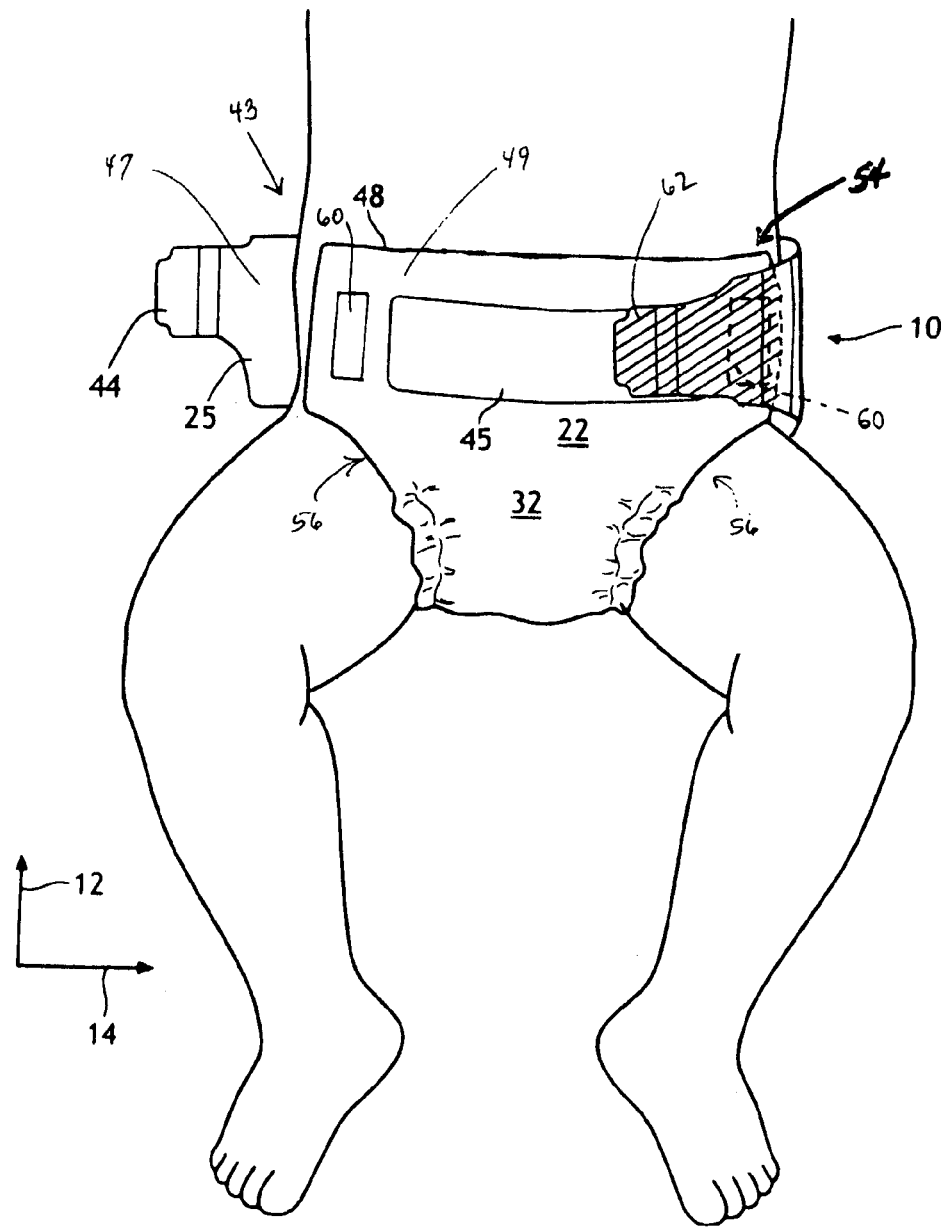
FIG. 3 representatively illustrates the diaper of FIGS. 1 and 2 in a partially fastened condition on an infant.

FIGS. 1, 2, and 3 representatively illustrate an exemplary diaper 10 of the present invention. FIG. 1 representatively illustrates the diaper 10 in an unfastened condition with portions of the diaper 10 cut away to illustrate underlying structures. The surface of the diaper which contacts the wearer is facing the viewer in FIG. 1. FIG. 2 representatively illustrates the diaper 10 in an unfastened condition with the surface of the diaper oriented towards the clothing of the wearer facing the viewer. FIG. 3 representatively illustrates the diaper 10 in a partially fastened condition on an infant.

Referring now to FIGS. 1, 2, and 3, the diaper 10 has a longitudinal direction 12 and a lateral direction 14. In the longitudinal direction 12, the diaper 10 defines a front portion 22, a back portion 24, and a crotch portion 26 connecting the front portion 22 and the back portion 24. The diaper 10 includes a bodyside liner 30, an outer cover 32 and an absorbent core 34 located between the bodyside liner 30 and the outer cover 32. The front portion 22 may include, at least partially, one or more front ears 23. The back portion 24 may include, at least partially, one or more back ears 25. The front ears 23 and/or the back ears 25 may be formed from extensions of the bodyside liner 30, the outer cover 32, combinations of both the bodyside liner 30 and the outer cover 32, or by the addition of one or more separate components as is known in the art.

The diaper 10 may also include a fit system 43. The fit system 43 may include one or more back fasteners 44, one or more front fasteners 45, and one or more friction elements 60. Portions of the fit system 43 may be included in the front portion 22, the back portion 24, or both. The fit system 43 is adapted to secure the diaper 10 about the waist of a wearer and maintain the diaper 10 in place during use. When secured, the diaper 10 defines a waist opening 54 and a pair of leg openings 56.

The diaper 10 may also include a surge portion 33 joined to the absorbent core 34 and/or the bodyside liner 30. As used herein, reference to a front portion 22 refers to that part of the diaper which is generally located on the front of a wearer when in use. Reference to the back portion 24 refers to the portion of the diaper generally located at the back of the wearer when in use, and reference to the crotch portion 26 refers to that portion which is generally located between the legs of the wearer when in use.

The crotch portion 26 has opposite longitudinal side portions 28 which may include a pair of elasticized, longitudinally-extending leg cuffs 36. The leg cuffs 36 are generally adapted to fit about the legs of a wearer in use and serve as a mechanical barrier to the lateral flow of body exudates. The leg cuffs 36 may be elasticized by a pair of leg elastics 38. The diaper 10 may further include a front waist elastic 40 and/or a back waist elastic 42.

The back portion 24 includes a back waist area 47 and may have a straight back waist edge 46, an arcuate back waist edge 46, or a back waist edge 46 cut in other shapes as are known in the art. The front portion 22 includes a front waist area 49 and may have a straight front waist edge 48, an arcuate front waist edge 48, or a front waist edge 48 cut in other shapes as are known in the art.

The diaper 10 may also include a pair of containment flaps 52 that may extend longitudinally along the diaper 10 and may also be adapted to provide a barrier to the flow of body exudates. It should be recognized that individual components of the diaper 10 may be optional depending upon the intended use of the diaper 10.

The bodyside liner 30 of the diaper 10, as representatively illustrated in FIG. 1, suitably presents a body facing surface which is intended to be worn adjacent the body of the wearer and is compliant, soft feeling and nonirritating to the wearer's skin. Further, the bodyside liner 30 may be less hydrophilic than the absorbent core 34 and may be sufficiently porous to be liquid permeable. A suitable bodyside liner 30 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 30 is suitably employed to help isolate the wearer's skin from fluids held in the composite absorbent core 34.

The outer cover 32 of the diaper 10, as representatively illustrated in FIG. 2, suitably presents a garment facing surface which is intended to be worn adjacent the clothing of the wearer. The outer cover 32 may include a polyethylene film. Alternative constructions of the outer cover 32 may comprise a woven or non-woven fibrous web layer which has been totally or partially constructed or treated to impart a desired level of liquid impermeability to selected regions of the outer cover that are adjacent or proximate the absorbent core 34. For example, a clothlike outer cover may be composed of polypropylene spunbond fabric which is laminated and thermally bonded to a stretch-thinned polypropylene film. The outer cover 32 may optionally include a microporous, "breathable" material which permits vapors to escape from the diaper 10 while still preventing liquid exudates from passing through. For example, the outer cover 32 may be composed of a microporous polymer film or a nonwoven fabric which has been coated or otherwise treated to impart a desired level of liquid impermeability. The outer cover 32 can also be embossed or otherwise provided with a matte finish to exhibit a more aesthetically pleasing appearance. The size of outer cover 32 is typically determined by the size of the diaper 10 and the exact diaper design selected.

The bodyside liner 30 and outer cover 32 are generally joined in facing relationship with the absorbent core 34 located therebetween. The bodyside liner 30 and the outer cover 32 may be joined to each other around the outer periphery of the diaper 10 by any means known to those skilled in the art such as adhesive bonds, sonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

The leg cuffs 36 are suitably formed by portions of the outer cover 32, and/or bodyside liner 30, which extend beyond the longitudinal sides of the absorbent core 34. Alternatively, the leg cuffs 36 can be formed from separate materials joined to the outer cover 32 and/or bodyside liner 30. In some embodiments, the leg cuffs 36 may have an arcuate shape resulting from a leg cut out 37. In other embodiments, the leg cuffs 36 may have a generally straight shape.

The leg cuffs 36 may include leg elastics 38. Front waist elastics 40 and/or back waist elastic 42 may also be provided. The leg elastics 38 may be arranged to draw and hold the diaper 10 against the legs of the wearer. The waist elastics 40 and 42 may also be arranged to draw and hold the diaper 10 against the wearer, particularly at the waist. Materials suitable for use in forming leg elastics 38 and/or waist elastics 40 and 42 are known to those skilled in the art. Exemplary of such materials are strands or ribbons of a polymeric, elastomeric material which are adhered to the diaper 10 in a stretched position, or which are attached to the diaper 10 while the diaper 10 is pleated, such that elastic constrictive forces are imparted to the diaper 10. The leg elastics 38 and/or waist elastics 40 and 42 may have any configuration which provides the desired performance. The leg elastics 38 may be generally straight or optionally curved to more closely fit the contours of the legs and buttocks of the wearer and better contain bodily exudates. The leg elastics 38 and/or waist elastics 40 and 42 may be attached to the diaper 10 in any of several ways which are well known to those skilled in the art. For example, the elastics may be joined to the diaper 10 by ultrasonic bonding, thermal bonding, adhesive bonding, and the like, and combinations thereof.

The front ears 23 and/or the back ears 25 are suitably formed by portions of the outer cover 32, and/or bodyside liner 30, which extend beyond the longitudinal sides of the absorbent core 34. For example, in FIGS. 1, 2, and 3, the front ears 23 are illustrated as portions of both the outer cover 32 and the bodyside liner 30. Alternatively, the front ears 23 and/or back ears 25 may be formed from separate materials which are joined to the outer cover 32 and/or bodyside liner 30. For example, in FIGS. 1, 2, and 3, the back ears 25 are illustrated as separate pieces of material attached to the bodyside liner 30.

The front ears 23 and/or the back ears 25 of the present invention may comprise one or more materials joined together to form a composite ear as is well known in the art. One or more of the materials may be elastomeric. Elastomeric ears can be formed from any type of an elastomeric material capable of performing as described herein. Generally, the elastomeric material will be stretchable in at least one direction. Preferably, the elastomeric material will be stretchable in two directions. When the elastomeric material is stretchable in a single direction, the stretch direction of the elastomeric material will be oriented so as to provide elastomeric forces which tend to pull the front and back portions of the diaper towards one another such that the diaper is maintained about the waist of a wearer.

The elastomeric material may be an inherently elastomeric material, that is, one which is formed in an elastomeric state, or may be rendered elastomeric through processing subsequent to formation. For example, the elastomeric material may be heat or pressure activated. In particular embodiments of the invention, portions of the ears may comprise an elastomeric material, such as a stretch-bonded-laminate (SBL) material, a neck-bonded-laminate (NBL) material, an elastomeric film, an elastomeric foam material, or the like, or combinations thereof.

In some embodiments, the back fasteners 44 may be joined to the back portion 24, the back ears 25 or both and the front fasteners 45 may be joined to the front portion 22, the front ears 23, or both. The back fasteners 44 may be one or more discrete pieces of material joined to the diaper 10 and adapted to align with and work in conjunction with the front fasteners 45, which may be one or more discrete pieces of material joined to the diaper 10. For example, the front fastener 45 may be a piece of loop material joined with the outer cover 32 in the front portion 22 and configured to engage hook-type back fasteners 44 when the diaper 10 is wrapped about the waist and legs of a user as illustrated in FIG. 3.

Alternatively, the one or more front fasteners 45 may include portions of the outer cover 32, the bodyside liner 30, or both and be configured to engage hook-type back fasteners 44. For example, the outer cover 32 may be configured to include a non-woven material suitable for engagement with hook materials. In such an embodiment, hook-type fasteners 44 may be located at the back ears 25 and wrapped around the waist of the wearer. The hook-type fasteners 44 may then be engaged directly with the nonwoven outer cover 32 to join the back portion 24 with the front portion 22 and secure the diaper 10 about the waist of the wearer.

Alternatively, the one or more front fasteners 45 may include hook-type fasteners and the one or more back fasteners 44 may include one or more complementary loop-type fasteners. In various embodiments, the one or more back fasteners 44 and/or the one or more front fasteners 45 may comprise any suitable materials adapted to join the back portion 24 to the front portion 22 of the diaper 10 thus securing the diaper about the waist of a wearer. Suitable fastening materials include hook and loop materials, adhesives, adhesive tapes, cohesives, snaps, buttons, latches, hooks, and the like, and combinations thereof.

The absorbent core 34 is positioned between the bodyside liner 30 and the outer cover 32 to form the diaper 10. The absorbent core 34 is generally conformable and capable of absorbing and retaining body exudates. The absorbent core 34 may include superabsorbent material, staple fibers, binder fibers, and the like, and combinations thereof as is known in the art. The absorbent core 34 may have any of a number of shapes and sizes. For example, the composite absorbent core may be rectangular, I-shaped or T-shaped. The size and absorbent capacity of the absorbent core 34 should be compatible with the size of the intended wearer and the fluid loading imparted by the intended use of the diaper.

In various embodiments, the surge portion 33 serves to quickly collect and temporarily hold discharged fluids and then to eventually release the fluids into the absorbent core 34. Various woven and nonwoven materials can be used to construct the surge portion 33. For example, the surge portion 33 may be a layer of a spunbonded or meltblown web of polyolefin fibers. The surge portion 33 may also be a bonded carded web of natural and synthetic fibers. The surge portion 33 may be a substantially hydrophobic material and, optionally, can be treated with a surfactant or otherwise to impart a desired level of wettability and hydrophilicity.

Containment flaps 52 may be connected to the bodyside liner or other components as is well known in the art. Suitable configurations of the containment flaps 52 are described, for example, in U.S. Pat. No. 5,599,338 issued Feb. 4, 1997, to K. Enloe, the entirety of which is incorporated herein by reference where not contradictory.

The fit system 43 of the present invention includes one or more friction elements 60. In use, the friction elements 60 are located between the front portion 22 and the back portion 24 in the overlap regions 62. The overlap regions 62 are defined generally by the area wherein the back portion 24 overlaps the front portion 22 or the front portion 22 overlaps the back portion 24 when the diaper 10 is fastened about the waist of the wearer. The overlap regions 62 will vary slightly from user to user and application to application but generally includes portions of the front ears 23 and the back ears 25 that overlap one another when the diaper 10 is properly secured to a wearer of the size for which the diaper was designed. An exemplary overlap region 62 is highlighted by cross hash marks in FIG. 3. Placement of the friction elements 60 in the overlap regions 62 reduces radial shifting between the back waist area 47 and the front waist area 49. This reduction in shifting is believed to improve fit, comfort, aesthetics, and/or leakage by maintaining the diaper 10 in generally the original fastened position.

The shifting of the front portion 22 relative to the back portion 24 may occur in various extents in different locations within the overlap region 62. For example, the present inventors have observed that diapers shift by a greater amount in the portion of the overlap region 62 proximate the leg opening 56 as compared to the portion of the overlap region 62 proximate the waist opening 54. This shifting may be undesirable because of actual or perceived loss of fit. In other words, a user may initially attach the diaper 10 about the waist and legs of a wearer in a desired configuration to achieve a desired fit. However, after some use, the configuration may change for a variety of reasons and the actual and/or perceived fit may become less satisfactory. To minimize this effect, the present invention includes graduated friction elements in the overlap regions to selectively increase friction and minimize radial shifting.

In various embodiments, the friction elements 60 may have sufficient loft or resiliency such that a person perceives the elements as having a cushion effect when contacting the skin. Thus friction elements 60 may be configured to reduce irritation of the user's skin, even when in direct contact with the user's skin. Generally, friction elements 60 assist in maintaining the original secured position of front portion 22 of diaper 10 relative to the back portion 24 of diaper 10 through surface-to-surface friction, or shear forces, when in contact with outer cover 32, the liner 30, the front waist elastic 40, the back waist elastic 42, and/or other components located in the overlap regions 62.

In various embodiments, the friction elements 60 may be located in a front waist area 49, a back waist area 47, or both. For example, in some embodiments, the back waist area 47 of the diaper 10 may be defined, in part, by a back waist edge 46 and may include a back waist elastic 42. Likewise, in some embodiments, the front waist area 49 of the diaper 10 may be defined, in part, by a front waist edge 48 and may include a front waist elastic 40. The friction elements 60 may be located on the outer cover 32 in the front waist area 49 and may be positioned such that the upper portion 64 of the friction elements 60 contact the back waist elastic 42 and the lower portion 66 of the friction elements 60 contact the bodyside liner 30 when the back waist areas 47 are overlapped onto and fastened to the front waist areas 47 and the front waist edge 48 and the back waist edge 46 are aligned or are substantially aligned.

In various embodiments, the friction elements 60 may be made of any suitable material. For example, the friction elements 60 may be made of a foam material or other soft material having a high coefficient of friction. For example, a suitable material for friction element 60 is an open-cell flexible polyurethane foam or a reticulated foam. The foam material may have sufficient softness that, when contacting the skin of a wearer, the material does not red-mark the skin during normal usage.

As used herein, a foam material is "open-celled" if at least 60% of the cells in the foam structure that are at least 1 micrometer (µm) in size are in fluid communication with at least one adjacent cell. In one embodiment of the present invention, at least 80% of the cells in the foam structure that are at least 1 µm in size are in fluid communication with at least one adjacent cell.

As used herein, the term "reticulated foam", as it is commonly used among those skilled in the art, denotes solid foamed materials where substantially all intervening "window walls" or cell membranes have been removed from the cells of the foam, leaving a network consisting primarily of interconnected struts along the outlines of the cells formed during the foaming. Reticulated foams are thus distinct from foams in which the window walls are merely broken, or foams in which only the outermost window walls or skin have been removed by physical means. Reticulated foams, by virtue of their general lack of cell membranes, are highly permeable to gas and liquid alike, offering little resistance to fluid flow, indeed much less than those foams in which the cell membranes have been retained.

Other suitable foams and methods for manufacturing said foams are disclosed in U.S. patent application Ser. No. 11/413,876, filed on Apr. 27, 2006, and published as US20070099531, the entirety of which is incorporated herein by reference where not contradictory.

In one embodiment of the present invention, the foam layer may include an open-celled foam such as a melamine foam, a polyurethane foam, or other known open-celled foams. Such foam materials typically comprise rod-like struts forming a reticulated network that defines cells in the foam materials.

Melamine-based foams may include the foams currently manufactured by BASF, located in Ludwigshafen, Germany, under the BASOTECT® brand name. For example, BASOTECT® 2011, with a density of about 0.01 g/cm$^3$, may be used.

Examples of potentially useful reticulated foams include the polyurethane reticulated foams of Foamex, Inc., located in Linwood, Pa., such as foam SIF-60z; and, the reticulated foams of the following firms: Crest Foam Industries, Inc., located in Moonachie, N.J., including FilterCrest® reticulated foams; Scottfoam Corporation, located in Eddystone, Pa.; Swisstex, Inc., located in Greenville, S.C.; Recticell, located in Chicago, Ill.; and, the foams produced at Caligen Europe BV, located in Breda, the Netherlands, a subsidiary of British Vita PLC, located in Manchester, England.

Another suitable foam includes a polyurethane based open cell reticulated foam sold under the brand name VITA 5200 alv which may be obtained through Caligen Foam Limited having offices at Oldham Road, Middleton, Manchester, M242DB, United Kingdom.

Other open-celled foam materials may be suitable for use as friction elements, such as a layer of an aminoplast foam (e.g., foams made from urea-formaldehyde resins or melamine-formaldehyde resins), a phenolic foam such as a foam made from phenol-formaldehyde resins. In some embodiments, the foam layer may include a thermoset foam. The friction elements may include more than one kind of foam such as heterogeneous foam layers. Alternatively, two or more kinds of foam material may be blended or joined together during foam manufacture or existing foams may be laminated or otherwise joined together.

The friction elements may be cut, sliced, stacked, and/or folded to any desired thickness, and may be cut to be planar, sinusoidal, or to have other geometric features. In some embodiments, the friction elements may be sliced into layers having a thickness from about 0.5 mm to about 5 mm.

Other materials having similar properties and a high coefficient of friction can also be utilized. For example, a melt-blown nonwoven with fiber sizes less than 10 micrometers, having a basis weight of from 10 grams per square meter to 100 grams per square meter, formed from elastomeric polyethylene, such as Affinity 52800.02, manufactured by Dow Chemical Co. of Midland, Mich., may also be utilized for friction element 60. In some embodiments, the friction elements may be made of high coefficient of friction films. For example, a coextruded film with a thickness of about 0.75 mils and composed of about 75% by weight layer of polyethylene and about 25% by weight layer of polyolefin. A suitable coextruded film is identified by the identification number XC2-21-826.1 and is available from Consolidated Thermoplastics Company of Chippewa Falls, Wis. Another suitable film composition includes a polyolefin elastomer and adhesive laminated to non-stretchable nonwoven substrate.

In various embodiments, the friction elements 60 define an upper portion 64 oriented towards the waist opening 54 (i.e., the front waist edge 48 or the back waist edge 46) and a lower portion 66 oriented towards the leg opening 56 (i.e., the leg cut out 37). In any of the embodiments disclosed herein, the entire upper half of the friction elements 60 may define the upper portion 64 and the entire lower half may define the lower portion 66. As used herein, the upper half is separated by the lower half by a lateral direction centerline 80. The lateral direction centerline 80 is parallel to the lateral direction 14 and divides the length of the friction element 60 in half as measured in the longitudinal direction 12.

In various embodiments, the upper portion 64 is adapted to provide less resistance to slippage as compared to the lower portion 66. In various embodiments, the entire upper portion 64 (upper half) is adapted to provide less resistance to slippage as compared to the entire lower portion 66 (lower half). The difference in resistance to slippage between the upper portion 64 and the lower portion 66 may be achieved through various means such as by varying the relative concentration of surface treatment applied to the upper and lower portions, by varying the relative thickness of the upper and lower portions, by varying the relative area or shape of the upper and lower portions, or combinations thereof.

Figure 4:
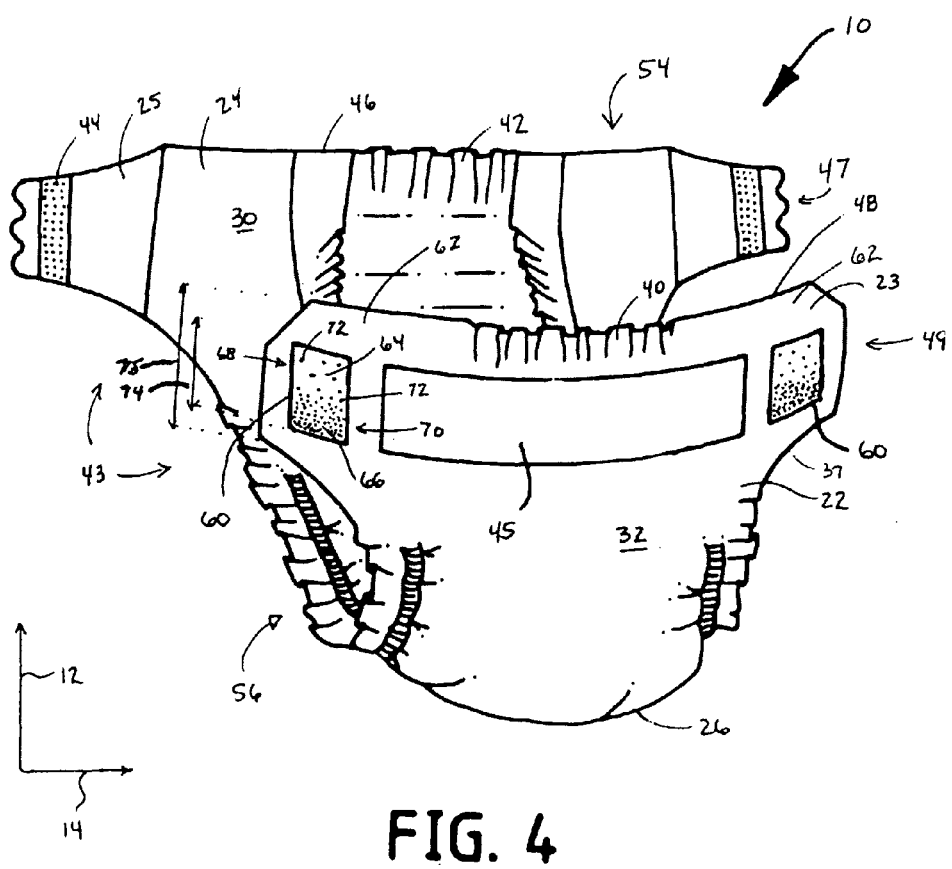
FIGS. 4-6, 9, and 11 representatively illustrate various exemplary embodiments of the present invention.

Referring now to FIG. 4, an exemplary diaper 10 is illustrated with a fit system 43. The fit system 43 includes back fasteners 44 and a front fastener 45. The fit system 43 also includes two friction elements 60 located in the front waist area 49 and joined to the outercover 32. The diaper 10 defines a waist opening 54 and a pair of leg openings 56 when the back fasteners 44 are joined with front fastener 45 in a fastened condition. The portions of the back waist area 47 that lay over the front waist area 47 in the fastened condition define overlap regions 62.

In various embodiments, and as illustrated in FIG. 4, the upper portion 64 of friction elements 60 may have a first concentration 68 of a surface treatment 72 resulting in a first coefficient of friction and the lower portion 66 of friction elements 60 may have a second concentration 70 of surface treatment 72 resulting in a second coefficient of friction. In various embodiments, the second concentration 70 is greater than the first concentration 68. In various embodiments, the second coefficient of friction is greater than the first coefficient of friction. In some embodiments, the upper portion 64 of the friction elements 60 may have a first surface treatment having a first coefficient of friction and the lower portion 66 of the friction elements 60 may have a second surface treatment having a second coefficient of friction that is greater than the first coefficient of friction. In some embodiments, the upper portion 64 of the friction elements 60 may have no surface treatment while the lower portion 66 has surface treatment 72.

In some embodiments, the first and/or second surface treatment 72 may be any suitable skid resistant coating added to friction element 60. For example, the surface treatment 72 may be formed from the following groups of materials: ethylene vinyl acetate copolymers applied as a hot melt or as a water based coating having at least 28% vinyl acetate; polyvinyl acetate in water-based emulsions; styrene-butadiene in an emulsion or as a hot melt; cellulose acetate butyrate in a hot melt; ethyl cellulose blended with a plasticizer and a resin; acrylics in an emulsion system that are not blended; synthetic rubber (KRATON® block copolymers having elastomeric and styrenic blocks), rubber, resin, plasticizer blends and hot melts including polyethylene (alone or blended) and polyamides among others.

In some embodiments, the surface treatment 72 may include films or coatings. For example, friction element 60 may include a coextruded film with a thickness of about 0.75 mils. The coextruded film may be composed of about 75% by weight layer of polyethylene and about 25% by weight layer of polyolefin. A suitable coextruded film is identified by the identification number XC2-21-826.1 and is available from Consolidated Thermoplastics Company of Chippewa Falls, Wis.

In some embodiments, the surface treatment 72 may be a low-tack adhesive or polymer wax. The surface treatment 72 may be applied utilizing numerous methods, for example spray nozzles, glue guns, bead applicators, extruders, gravure printing, flexographic printing, ink-jet printing, coating, and the like.

The first concentration 68 and/or the second concentration 70 of the surface treatment 72 may be at any suitable add-on. For example, the first concentration 68 and/or the second concentration 70 may be less than 100 gsm, alternatively less than 50 gsm, alternatively less than 30 gsm or alternatively less than 25 gsm. In some embodiments, the first concentration 68 and/or the second concentration 70 may be greater than 1 gsm, alternatively greater than 5 gsm, alternatively greater than 10 gsm or alternatively greater than 15 gsm.

In various embodiments, the upper portion 64 and/or the lower portion 66 of the friction elements 60 may have any suitable coefficient of friction. For example, the upper portion 64 and/or the lower portion 66 of the friction elements 60 may have a coefficient of friction of at least 2.0 as measured according to the test method described herein. In some embodiments, the upper portion 64 and/or the lower portion 66 of the friction elements 60 may have a coefficient of friction of about 2.2. In some embodiments, the upper portion 64 and/or the lower portion 66 of the friction elements 60 may have a coefficient of friction ranging from 2.7 to 8.2. In some embodiments, the upper portion 64 and/or the lower portion 66 of the friction elements 60 may have a coefficient of friction of about 7.6. In some embodiments, the upper portion 64 may have a lesser coefficient of friction value as compared to the lower portion 66. In some embodiments, the upper portion 64 may have the same coefficient of friction value as the lower portion 66. In other embodiments, the upper portion 64 may have a greater coefficient of friction value as compared to the lower portion 66. The relative coefficients of friction may be selected by using different materials and/or different surface treatments, and/or different concentrations of surface treatments.

Figure 5:
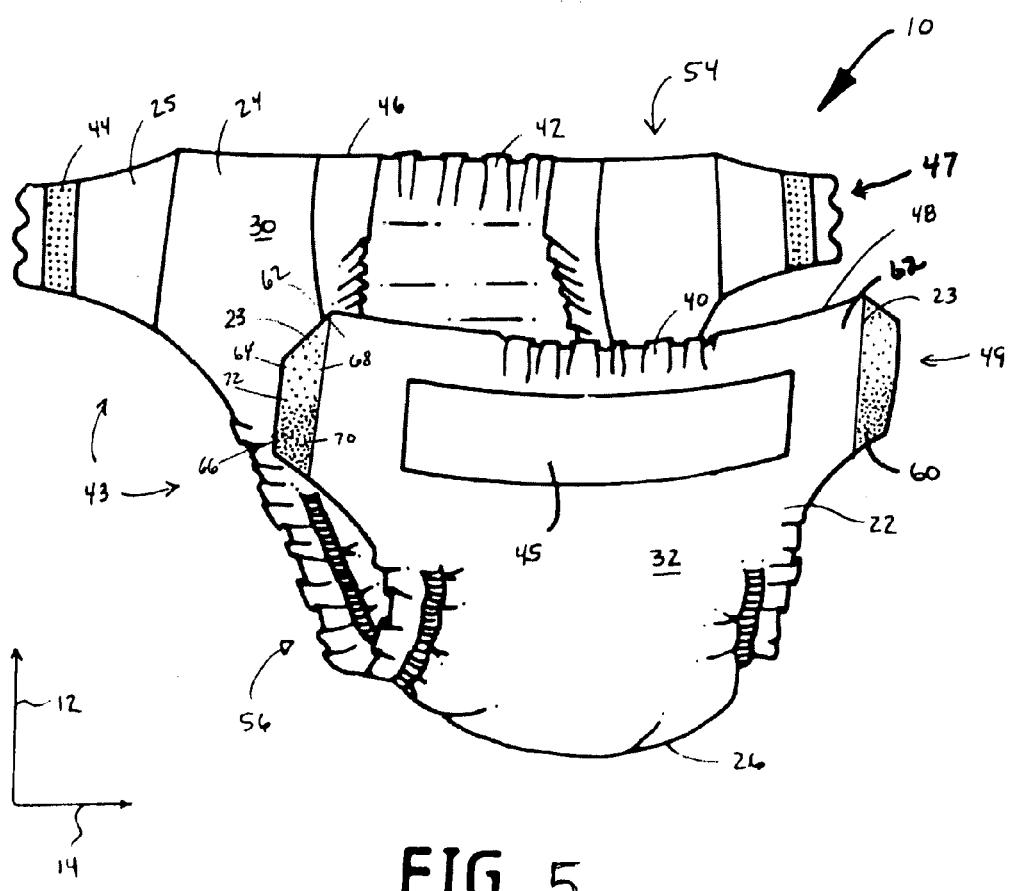

Referring now to FIG. 5, an exemplary diaper 10 is illustrated with a fit system 43. The fit system 43 includes two back fasteners 44 and one front fastener 45. The fit system 43 also includes two friction elements 60 joined to the bodyside liner 30 and/or the outercover 32 in the front waist area 49. The diaper 10 defines a waist opening 54 and a pair of leg openings 56 when the back fasteners 44 are joined with front fastener 45 in a fastened condition. The portions of the back waist area 47 that lay over the front waist area 47 in the fastened condition define overlap regions 62. In this embodiment, the upper portions 64 of the friction elements 60 have a first concentration 68 of a surface treatment 72 and the lower portions 66 of the friction elements 60 have a second concentration 70 of the surface treatment 72 which is greater than the first concentration 68.

Figure 6:
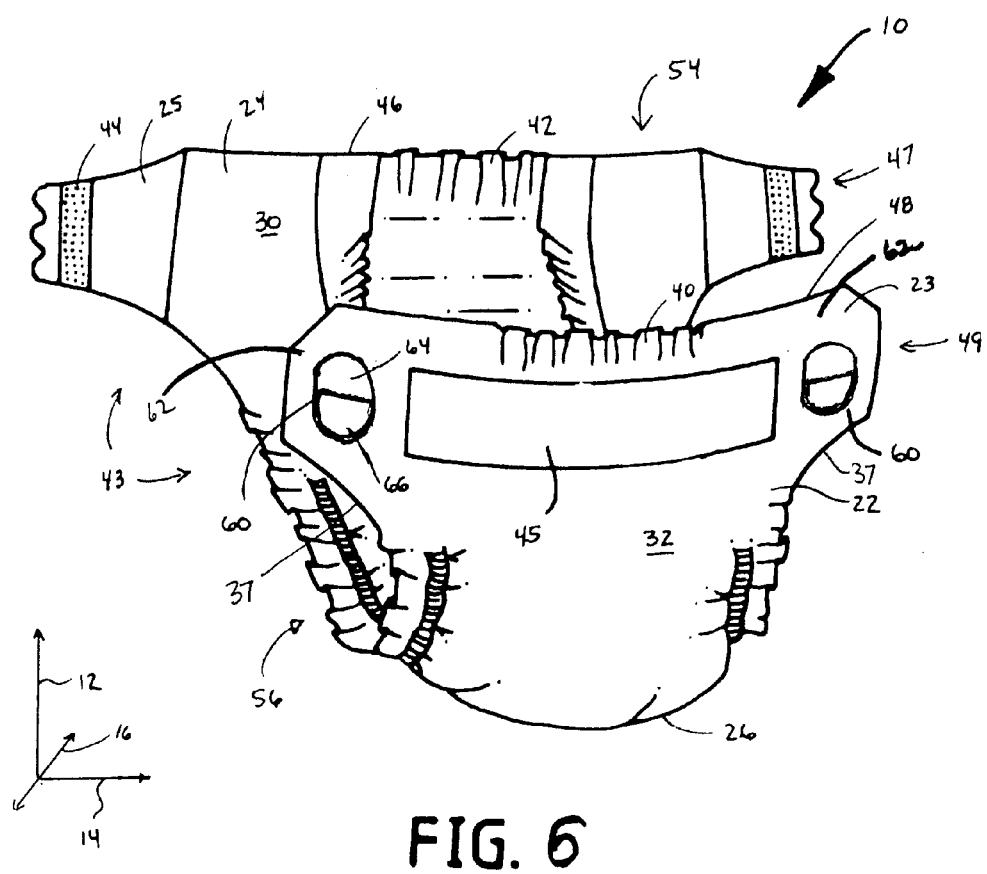

Referring now to FIG. 6, an exemplary embodiment of the present invention is illustrated. Diaper 10 is shown with a fit system 43. The fit system 43 includes two back fasteners 44, a front fastener 45, and two friction elements 60. The back fasteners 44 are located in a back waist area 47 and the front fastener 45 is located in a front waist area 49. The back fasteners 44 and the front fastener 45 are adapted to secure the diaper 10 about the waist of a wearer to define a waist opening 54, a pair of leg openings 56, and a pair of overlap regions 62. The friction elements 60 are located in the overlap regions 62 and are adapted to provide friction between the front waist area 49 and the back waist area 47 in the overlap regions 62 when the back waist area 47 overlaps the front waist area 49 in the fastened condition. The friction elements 60 have an upper portion 64 oriented towards the waist opening 54 (i.e., the front waist edge 48) and a lower portion 66 oriented towards the leg opening 56 (i.e., the leg cut out 37). In this embodiment, the upper portion 64 has a first thickness 76 as measured in a z-direction 16 and the lower portion 66 has a second thickness 78 as measured in the z-direction 16 which is greater than the first thickness 76.

In various embodiments, the first thickness 76 and the second thickness 78 may be any suitable value. For example, the first thickness 76 may be 0.1 to 3 mm and the second thickness 78 may be 2 to 5 mm. In some embodiments, the friction elements 60 may have a stepped thickness, a tapered thickness, an irregular thickness, or combinations thereof.

Figures 7A, 7B, 8:
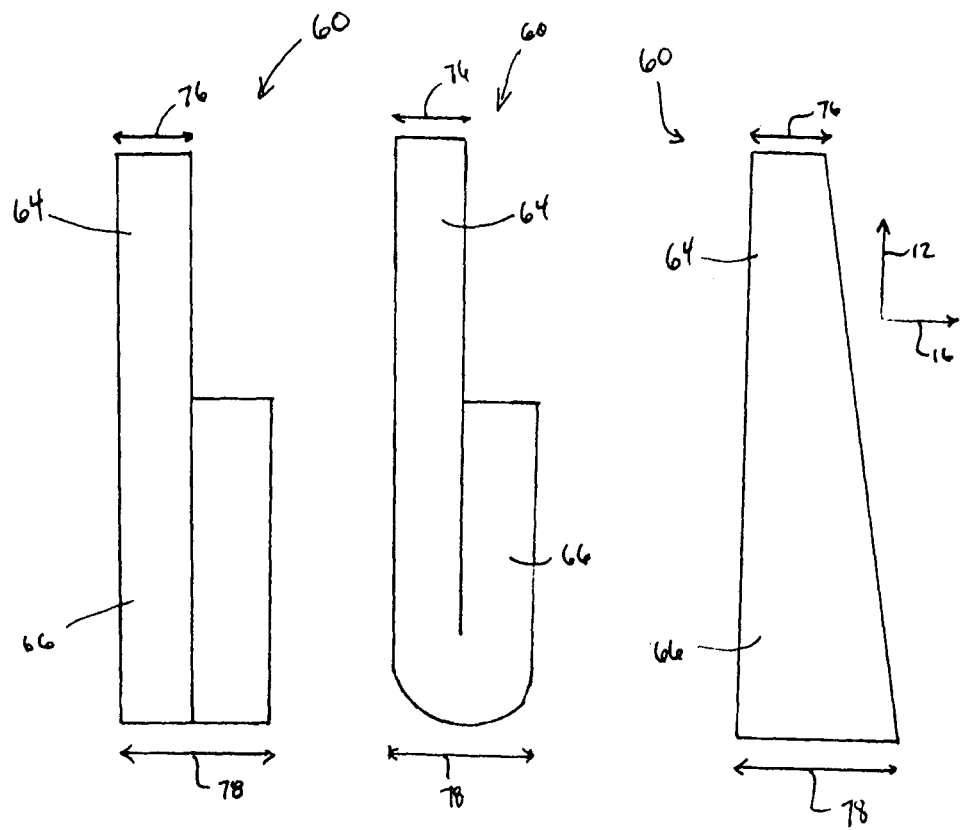
FIGS. 7a, 7b, and 8 representatively illustrate enlarged side views of exemplary embodiments of various friction elements.

For example, FIG. 7a representatively illustrates an enlarged side view of a friction element 60 having a stepped thickness. Specifically, the friction element 60 has an upper portion 64 having a first thickness 76 and a lower portion 66 having a second thickness 78. As illustrated, the second thickness 78 is greater than the first thickness 76. In some embodiments, the upper portion 64 may include a single layer of material and the lower portion 66 may include more than one layer of material as illustrated. In other embodiments, the upper portion 64 and the lower portion 66 may be a single layer of material but may be cut or otherwise manufactured to have different thicknesses.

In another example, FIG. 7b representatively illustrates an enlarged side view of a friction element 60 having a stepped thickness. Specifically, the friction element 60 has an upper portion 64 having a first thickness 76 and a lower portion 66 having a second thickness 78. As illustrated, the second thickness 78 is greater than the first thickness 76. In this embodiment, the upper portion 64 includes a single layer of material and the lower portion 66 includes the material folded over onto itself to provide a second layer of material.

In another example, FIG. 8 representatively illustrates an enlarged side view of a friction element 60 having a tapered thickness. Specifically, the friction element 60 has an upper portion 64 having a first thickness 76 and a lower portion 66 having a second thickness 78. As illustrated, the second thickness 78 is greater than the first thickness 76. The greater second thickness 78 uniformly tapers towards the lesser first thickness 76 in the illustrated embodiment. However, in various embodiments, the tapered thickness may not be uniform.

Figure 9:
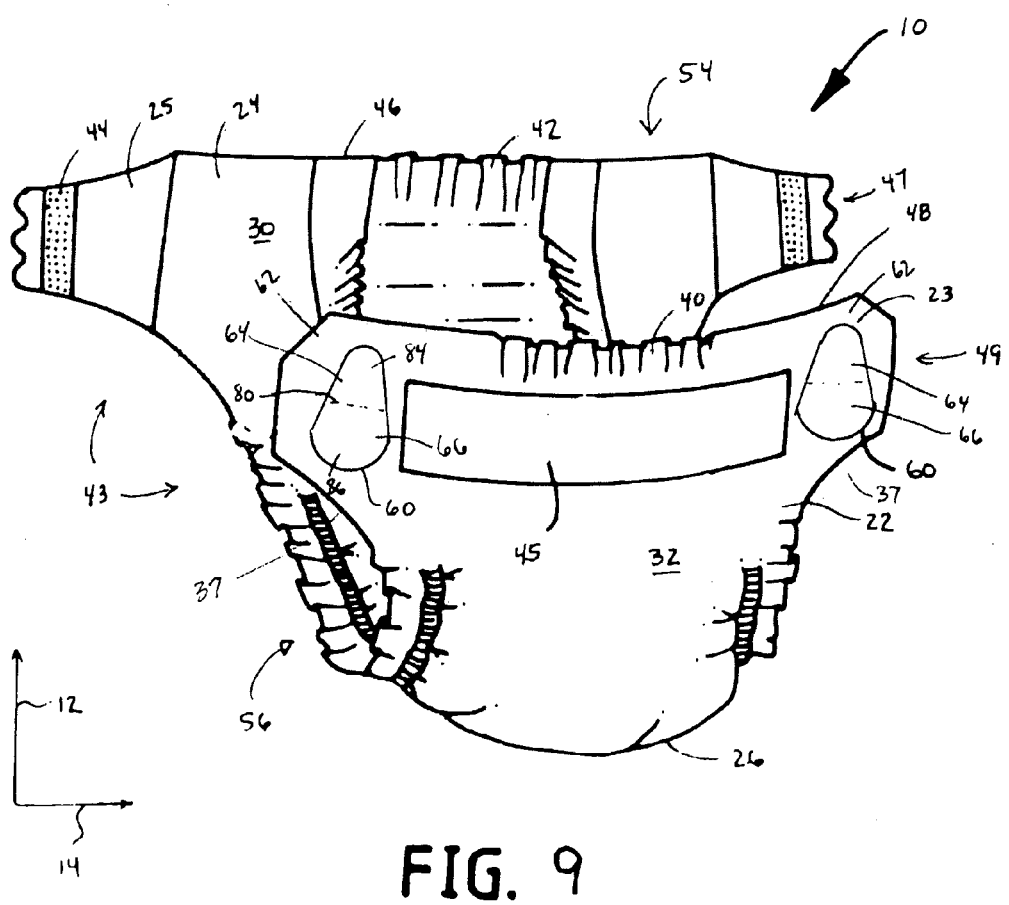

Referring now to FIG. 9, an exemplary embodiment of the present invention is illustrated. Specifically, a diaper 10 includes a fit system 43. The fit system 43 includes two back fasteners 44, a front fastener 45, and two friction elements 60. The front fastener 45 is located in the front waist area 49 and the back fasteners 44 are located in the back waist area 47. The back fasteners 44 are adapted to secure the diaper 10 about the waist of a wearer to define a waist opening 54, a pair of leg openings 56, and a pair of overlap regions 62. The friction elements 60 are located on the outercover 32 in the front waist area 49 in the overlap regions 62. The friction elements 60 are adapted to provide friction between the front waist area 49 and the back waist area 47 in the overlap regions 62 when the back waist area 47 overlaps the front waist area 49 in the fastened condition.

Figure 10:
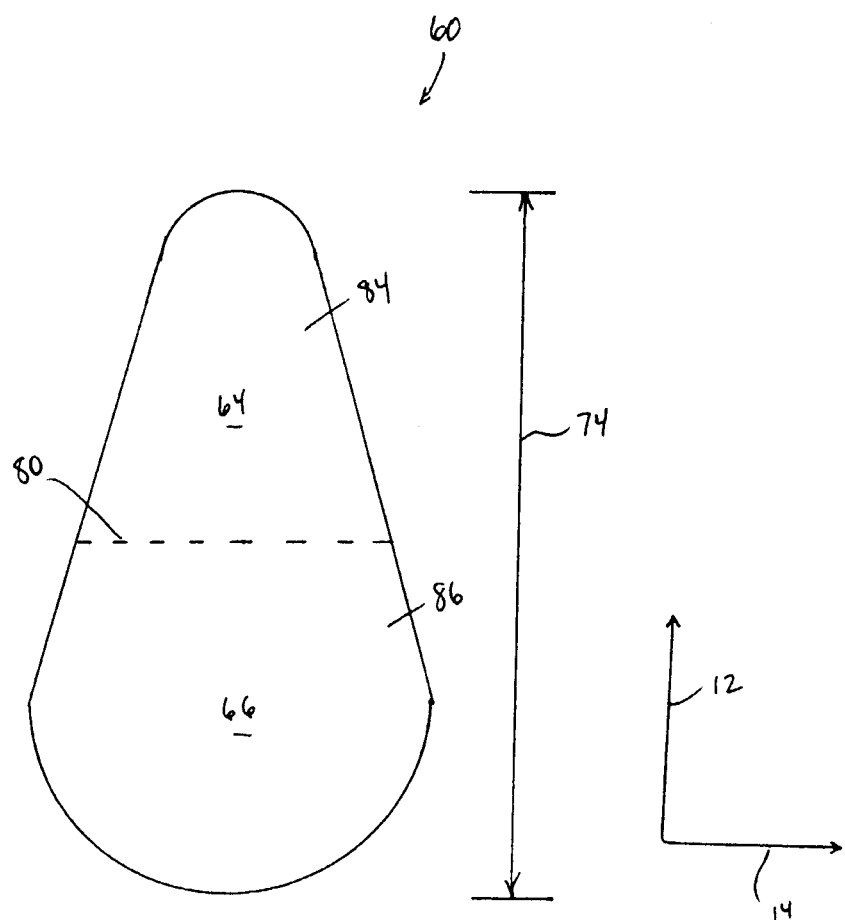
FIG. 10 representatively illustrates an enlarged view of the exemplary friction element of FIG. 9.

Referring now to FIG. 10, one of the friction elements 60 of FIG. 9 is enlarged to show greater detail. The friction elements 60 have a length 74 as measured in the longitudinal direction 12. The friction elements 60 also have a lateral direction centerline 80. The lateral direction centerline 80 is parallel to the lateral direction 14 and divides the friction element length 74 in half as measured in the longitudinal direction 12. The lateral direction centerline 80 defines the upper portion 64 and the lower portion 66. The upper portions 64 of the friction elements 60 are oriented towards the waist opening 54 (i.e., the front waist edge 48). The lower portions 66 of the friction elements 60 are oriented towards the leg opening 56 (i.e., the leg cut out 37). The entire upper portion 64 defines a first surface area 84 and the entire lower portion 66 defines a second surface area 86. In the illustrated embodiment, the second surface area 86 is greater than the first surface area 84.

Figure 11:
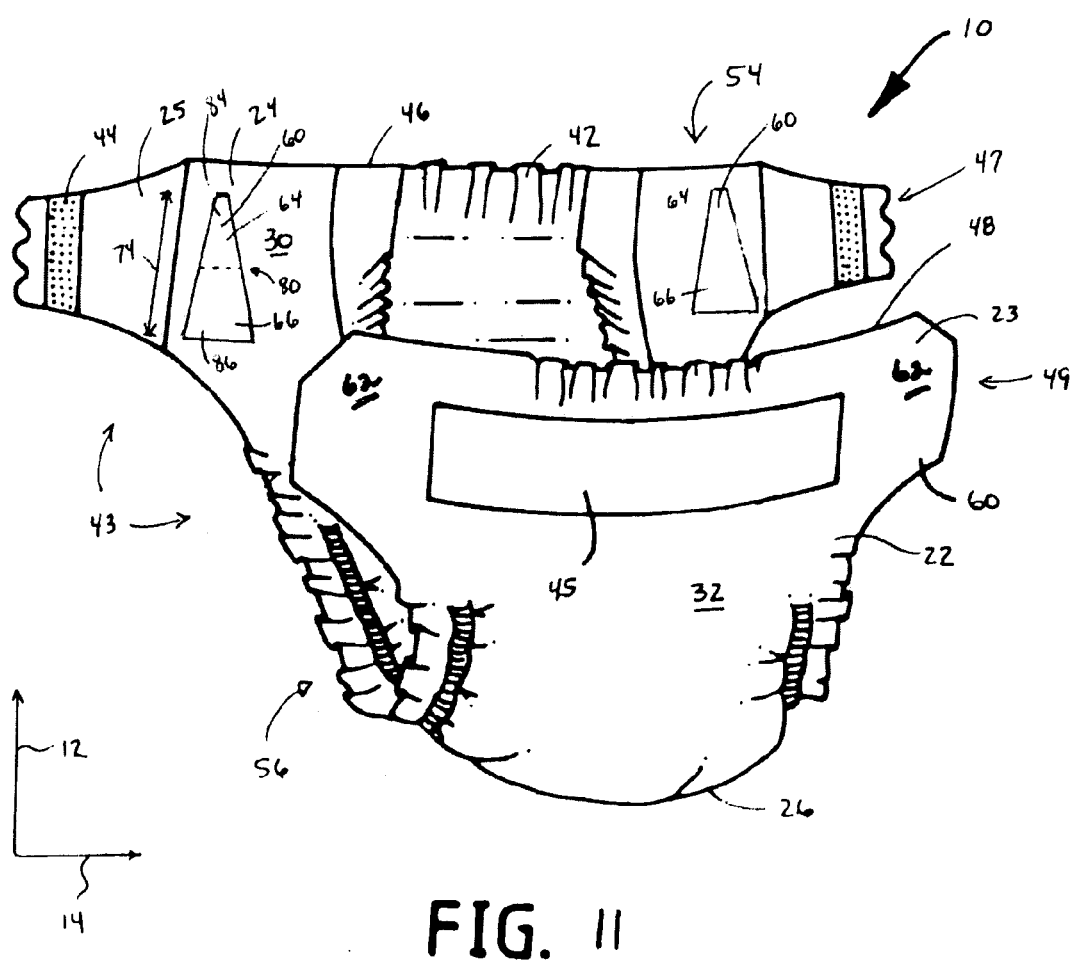

Referring now to FIG. 11, an exemplary embodiment of the present invention is illustrated. Specifically, a diaper 10 includes a fit system 43. The fit system 43 includes two back fasteners 44, a front fastener 45, and two friction elements 60. The front fastener 45 is located in the front waist area 49 and the back fasteners 44 are located in the back waist area 47. The back fasteners 44 are adapted to secure the diaper 10 about the waist of a wearer to define a waist opening 54, a pair of leg openings 56, and a pair of overlap regions 62.

The friction elements 60 are located on the liner 30 in the back waist area 47. The friction elements 60 are adapted to provide friction between the front waist area 49 and the back waist area 47 in the overlap regions 62 when the back waist area 47 overlaps the front waist area 49 when the diaper is in a fastened condition. The friction elements 60 have a length 74 as measured in the longitudinal direction 12. The friction elements 60 also have a lateral direction centerline 80. The lateral direction centerline 80 is parallel to the lateral direction 14 and divides the friction element length 74 in half and defines an upper portion 64 and a lower portion 66. The upper portion 64 is oriented towards the waist opening 54 (i.e., the back waist edge 46). The lower portions 66 of the friction elements 60 are oriented towards the leg opening 56 (i.e., the leg cut out 37). The entire upper portion 64 defines a first surface area 84 and the entire lower portion 66 defines a second surface area 86. In the illustrated embodiment, the second surface area 86 is greater than the first surface area 84.

In various embodiments, the first surface area 84 may be 100 mm² to 300 mm² and the second surface area 86 may be 200 to 800 mm². In various embodiments the first surface area 84 and/or the second surface area 86 and/or the friction element 60 may have any suitable shape and or size. For example, in some embodiments, the friction elements may be generally circular, triangular, elliptical, rectangular, irregular, or any other geometric shape, or the like, or combinations thereof. In some embodiments, the friction elements 60 may have a raindrop shape like those illustrated in FIGS. 9 and 10.

In various embodiments, the waist opening 54 and the leg openings 56 define a side coverage length 75 as measured in the longitudinal direction 12. (See FIG. 4). In some embodiments, the friction elements 60 have a length 74 as measured in the longitudinal direction 12 and the friction element length 74 is at least 50% of the side coverage length 75. In other words, in various embodiments, a single friction element may have an uninterrupted length 74 in the longitudinal direction 12 that is at least 50%, at least 60%, at least 70%, at least 80%, or at least 90% the length of the side coverage length 75. As used herein the term "side coverage" length refers to the distance as measured in the longitudinal direction 12 from the waist opening 54 to the leg opening 56 at the narrowest point and when the article is in the fastened condition.

As discussed above, the friction elements 60 provide resistance to shifting primarily through friction and shear forces and provide relatively low peel strength. Thus, in various embodiments, the friction elements 60 may have a peel value of less than 1000 grams as measured by the test method disclosed herein. In some embodiments, the friction elements 60 may have a peel value of less than 750 grams, less than 500 grams, less than 250 grams, and less than 100 grams. In some embodiments, the friction elements 60 may have a peel value of 0 grams.

Coefficient of Friction

The coefficient of friction of a sample may be obtained by placing the sample on a sliding table and moving the table and sample at a specified speed past a probe. The moving direction and distance are detected by a potentiometer as the displacement output voltage. Specifically, a Kawabata Evaluation System (KES) Surface Tester is used to measure the surface properties of the samples. This electronic instrument is available from KES Kato Tech Co. Ltd., having offices at 26 Karato-cho, Nisikujo, Minami-ku, Kyoto Japan, 601-8447. The KES surface tester includes a multi-wire probe consisting of 20 wires of 0.5 mm diameter each with a total width of 10 mm. The frictional force sensor of the probe is connected to a frictional force transducer with a linear differential transformer. The test speed is set at 1 mm/s with a normal force of 16 g. Double sided tape is used on the moving plate to hold the sample in place to reduce gathering when the probe swipes across the sample. Five samples are tested. The probe is cleaned with Isopropyl Alcohol after each test run to remove any residue. Two test parameters namely MIU and MMD are generated from this test and their definitions are listed below.

MIU—mean value of the coefficient of friction, dimensionless

MMD—mean deviation of MIU, dimensionless

The values are defined by $$MIU(\overline{\mu}) = \frac{1}{X}\int_0^x \mu dx$$

$$MMD = \frac{1}{X}\int_0^x |\mu - \overline{\mu}| dx$$

where
$\mu$=friction force divided by compression force
$\overline{\mu}$=mean value of $\mu$
x=displacement of the probe on the surface of specimen, cm
X=maximum travel used in the calculation, 2 cm MIU or COF values indicate the surface drag on the sample surface with higher MIU values indicating higher surface drag or tackiness. MMD is the mean deviation of MIU. Higher MMD values indicate higher variability and lower uniformity on the sample surface.

Peel Strength Test Method

Figure 12:
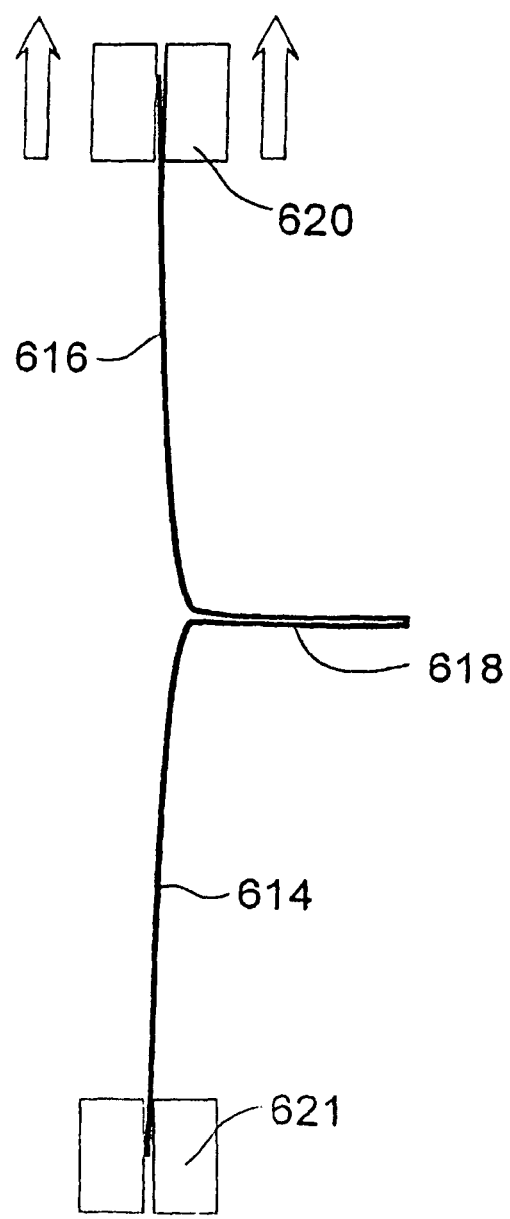
FIG. 12 representatively illustrates a test method for measuring peel values.

Peel strength may be measured by using a universal test machine (not shown) using the 180° peel configuration shown in FIG. 12, where the friction element 614 and nonwoven test fabric 616 are joined in an attachment zone 618 configured to be peeled apart as the remote ends of the strips 614 and 616, respectively, are moved away from each other as they are held in the jaws of an upper clamp 620 and a lower clamp 621 as shown. Using the universal testing machine (not shown) the force required to peel apart the attached friction elements 614 and nonwoven test fabric 616 may be measured. The nonwoven test fabric has a basis weight of 0.5 ounces per square yard (osy) and is composed of metallocene catalyzed polypropylene spunbond having a fiber denier of 2.0 and having a high density diamond (HDD) bond pattern. The crosshead speed for the peel testing is moved at 20 inches per minute. The attachment zone 618 has a length (overlap distance) of two inches, and a width of 3 inches (6 square inches total overlap area 612). The gauge length (distance between the upper and lower clamps 620 and 621, respectively) for the test set up is 1.5 inches. If the friction element 614 and the nonwoven test fabric 616 do not remain attached to allow testing, the peel strength is zero.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. An absorbent article comprising,
a lateral direction and a longitudinal direction,
an outer cover joined in facing relationship with a bodyside liner with an absorbent core located between the outer cover and the bodyside liner,
a fit system comprising fasteners and a friction element, wherein the fasteners are located in a front waist area and a back waist area and are adapted to fasten the article about the waist of a wearer to define a waist opening, a pair of leg openings, and a pair of overlap regions;

the friction element is located on the outer cover in the front waist area in at least one of the overlap regions and is adapted to provide friction between the front waist area and the back waist area in the overlap region, the friction element has an upper portion oriented towards the waist opening and a lower portion oriented towards the leg opening, the upper portion being separated from the lower portion by a lateral direction centerline which is parallel to the lateral direction of the absorbent article and which divides a length of the friction element in half as measured in the longitudinal direction of the absorbent article, the upper portion having applied to the friction element, a first concentration of surface treatment and the lower portion having applied to the friction element, a second concentration of surface treatment which is greater than the first concentration, and the friction element has a peel value of less than 1000 grams.

2. The absorbent article of claim 1 further comprising two friction elements; the fasteners include hook portions in the back waist area and loop portions in the front waist area, the two friction elements are located on the outer cover in the front waist area in the overlap region and have a peel value of less than 1000 grams.

3. The absorbent article of claim 1 wherein the surface treatment is selected from the group consisting of polyethylene polymer, low-tack adhesive, a cohesive, or a polymer wax.

4. The absorbent article of claim 1 wherein the friction element is made of reticulated open cell flexible polyurethane foam.

5. The absorbent article of claim 1 wherein the friction element comprises a foam material selected from the group consisting essentially of melamines; polyadehydes; polyurethanes; polyisocyanurites; polyolefins; polyvinylchloride; epoxy foams; ureaformaldehyde; latex foam; silicone foam; fluoropolymer foams; polystyrene foams; and, mixtures thereof.

6. The absorbent article of claim 1 wherein the waist opening and the leg openings define a side coverage length and wherein a single friction element is located in each overlap region and wherein each friction element has a friction element length that is at least 50% of the side coverage length.

7. The absorbent article of claim 1 wherein the upper portion has a first thickness and the lower portion has a second thickness which is greater than the first thickness.

8. An absorbent article comprising, a lateral direction, a longitudinal direction, and a thickness direction, an outer cover joined in facing relationship with a bodyside liner with an absorbent core located between the outer cover and the bodyside liner, a fit system comprising fasteners and a friction element, wherein the fasteners are located in a front waist area and a back waist area and are adapted to fasten the article about the waist of a wearer to define a waist opening, a pair of leg openings, and a pair of overlap regions;

the friction element is located on the outer cover in the front waist area in at least one of the overlap regions and is adapted to provide friction between the front waist area and the back waist area in at least one of the overlap regions, the friction element has an upper portion oriented towards the waist opening and a lower portion oriented towards the leg opening, the upper portion being separated from the lower portion by a lateral direction centerline which is parallel to the lateral direction of the absorbent article and which divides a length of the friction element in half as measured in the longitudinal direction of the absorbent article, the upper portion having a first thickness and the lower portion having a second thickness which is greater than the first thickness, and the friction element has a peel value of less than 1000 grams.

9. The absorbent article of claim 8 further comprising two friction elements; the fasteners including hook portions in the back waist area and loop portions in the front waist area, the friction elements being located on the outer cover in the front waist area in the overlap region and having a peel value of less than 1000 grams.

10. The absorbent article of claim 8 wherein the first thickness is 0.1 to 3 mm and the second thickness is 2 to 5 mm.

11. The absorbent article of claim 8 wherein the friction element comprises a foam material selected from the group consisting essentially of: melamines; polyadehydes; polyurethanes; polyisocyanurites; polyolefins; polyvinylchloride; epoxy foams; ureaformaldehyde; latex foam; silicone foam; fluoropolymer foams; polystyrene foams; and, mixtures thereof.

12. The absorbent article of claim 8 wherein the upper portion includes a single layer of material and the lower portion includes more than one layer of material.

13. The absorbent article of claim 8 wherein the thickness of the friction element is tapered and increases in thickness in a direction from the upper portion to the lower portion.

14. The absorbent article of claim 8 wherein the upper portion has a first coefficient of friction value and the lower portion has a second coefficient of friction value that is greater than the first coefficient of friction value.

15. The absorbent article of claim 8 wherein the waist opening and the leg openings define a side coverage length and wherein each friction element has a length and the friction element length is at least 50% of the side coverage length.

* * * * *